United States Patent [19]

Gui et al.

[11] Patent Number: 5,580,741

[45] Date of Patent: Dec. 3, 1996

[54] CHEMILUMINESCENCE IMMUNOASSAY FOR CHLORINATED AROMATIC COMPOUND DETECTION

[75] Inventors: John Y. Gui, Schenectady; Donald R. Berdahl, Scotia; Emily Y. Shu, Niskayuna; Joseph J. Salvo; Sandra F. Feldman, both of Schenectady, all of N.Y.

[73] Assignee: General Electric Company, Schenectady, N.Y.

[21] Appl. No.: 267,627

[22] Filed: Jun. 29, 1994

[51] Int. Cl.$^6$ ................................................. G01N 33/543
[52] U.S. Cl. .................... 435/7.93; 435/7.9; 435/968; 435/975; 436/545; 436/546; 436/815; 436/822; 436/828
[58] Field of Search .................... 435/7.1, 7.9, 7.92, 435/7.93, 964, 968, 969, 970, 975; 436/518, 532, 544, 545, 546, 815, 822, 828

[56] References Cited

U.S. PATENT DOCUMENTS

| | | |
|---|---|---|
| 4,120,945 | 10/1978 | Gutcho et al. . |
| 4,281,061 | 7/1981 | Zuk et al. . |
| 4,456,691 | 6/1984 | Stark et al. . |
| 5,128,244 | 7/1992 | Poland et al. . |
| 5,145,790 | 9/1992 | Mattingly et al. . |

OTHER PUBLICATIONS

Bandiera, S., et al. "Competitive Binding to the Cytosolic 2,3,7,8–tetrachlorodibenzo–p–dioxin Receptor." *Biochemical Pharmacology*,vol. 32, No. 24 (1983), pp. 3803–3813.
Bronstein, I. and A. Sparks. "Sensitive Enzyme Immunoassays with Chemiluminescent Detection." in: *Immunochemical Assays and Biosensor Technology for the 1990s* (American Society for Microbiology, 1992), pp. 229–250.
Ngai, K. M., et al. "Protein A antibody–capture ELISA (PACE): an ELISA format to avoid denaturation of surface–absorbed antigens." *Journal of Immunological Methods*, vol. 158 (1993), pp. 267–276.
Van Emon, J. M. and V. Lopez–Avila. "Immunochemical Methods for Environemntal Analysis." *Analytical Chemistry*, vol. 64, No. 2 (Jan. 15, 1992), pp. 79–88.

*Primary Examiner*—James C. Housel
*Assistant Examiner*—Prasad A. Murthy
*Attorney, Agent, or Firm*—Noreen C. Johnson; William H. Pittman

[57] ABSTRACT

A sensitive chemiluminescence immunoassay method for field detection of the presence or the amount of low chlorinated biphenyl compounds in a solution is disclosed. The assay has a five minute analysis time and a working range of detection as low as about 1 part per billion chlorinated biphenyl. Kits for the detection of chlorinated biphenyls are disclosed.

32 Claims, No Drawings

CHEMILUMINESCENCE IMMUNOASSAY FOR CHLORINATED AROMATIC COMPOUND DETECTION

FIELD OF THE INVENTION

The present invention relates to a method for detecting chlorinated aromatic compounds in the environment by immunoassay techniques. More specifically, it relates to detection and quantification of chlorinated biphenyls by chemiluminescence immunoassay.

BACKGROUND OF THE INVENTION

Chlorinated biphenyls are highly regulated compounds that have been accumulating in the environment over the years. There are many sites that have been contaminated with polychlorinated biphenyls (PCBs). Therefore, it is a high priority to have simple, rapid, and accurate methods for characterizing such sites and quantitively monitoring the remedial clean-up of such sites.

A current methodology for determining the presence or amount of polychlorinated biphenyls (PCBs) in a sample involves extracting the sample with an organic solvent and then using a gas chromatograph (GC) equipped with an electron capture detector (ECD) to analyze the extract. The problems encountered with this method are inherent to the analytical technique. For instance, the procedure is time-consuming and expensive since the GC/ECD runs only one sample at a time, requires about 40–60 minutes per test sample, and highly trained technical personnel are required to perform the testing and maintain the equipment. Even portable gas chromatograph methods are not rapid enough to dramatically lower the cost of analysis.

Another approach for detecting PCB pollutants in the environment is the utilization of immunoassay technology. Immunoassay offers a method which has similar sensitivity as gas chromatography, while being more rapid, simpler, and less expensive.

One such immunoassay that has been developed for detecting PCBs is radioimmunoassay. Radio immunoassays use reagents incorporating radioisotopes as tracers. The relative distribution of radiolabelled tracer and unlabelled PCBs from the sample allows determination of PCB concentrations in the sample. Iodine tracers are often used in the method to detect the PCBs.

Another immunoassay method is taught by U.S. Pat. No. 5,145,790 to Mattingly et al., for detecting the presence or amount of PCBs in a test sample using fluorescence polarization. The assay is performed by adding a known concentration of a tracer labeled with a detectable fluorescent moiety and a known concentration of a PCB-specific antibody to a test sample to form a mixture, incubating the mixture to form labeled tracer-antibody and PCB-antibody complexes. Free tracer and the tracer-antibody complexes are excited with polarized light and the polarization of the emitted light is measured to determine the presence or amount of tracer-antibody complexes formed, leading to a measure of the presence or amount of PCB in the test sample. Mattingly's method requires the use of a polarized light source and laboratory instrumentation.

While these immunoassay methods provide advantages over GC/ECD methods for screening of PCBs, they are subject to difficulties. When manually performed, these assay methods usually require an operator to carefully manage a number of reagents and operations. The outcome of a test is dependent upon successfully completing each operation. As a result, there are many opportunities for systematic errors.

Other difficulties with the above-mentioned immunoassay methods are that they require expensive equipment for automation, may involve the handling of radioactive materials, are not easily manipulated in field applications, and have a limited range of PCB detection.

Chemiluminescence is another method that is being used in immunoassays. Chemiluminescence is light emission that arises during the course of a chemical reaction. Light is produced when molecules, formed in an electronically excited state, decay to the ground state.

Chemiluminescent reactions provide a very sensitive detection system because no external light source is required as would be the case for fluorescence or colorimetric immunoassay methods. All the light reaching a detector originates from the chemical reaction with no contribution from scattered excitation radiation or background fluorescence from a substrate which limits the useful sensitivity of fluorescent detection. The instrumental background signal is essentially zero and hence the contribution of a single chemiluminescent reaction can be detected as a single photon.

The principle advantages of employing such reactions to monitor PCB immunoassay are that they are extremely sensitive and rapid. The labels are also relatively stable, have high specific activity and can take part in amplification reactions. This feature allows simple and rapid detection of trace levels of chlorinated biphenyls. Further, chemiluminescence analysis does not require complex instrumentation, but can be performed simply with a light intensity meter or films.

There is a need for a practical, effective chemiluminescence immunoassay method that detects PCBs in environmental samples quickly and accurately at field sites.

There is also a need to provide a sensitive test that detects low chlorine-content chlorinated biphenyls because of dechlorination processes in certain environmental conditions.

SUMMARY OF THE INVENTION

This invention fulfills these needs by providing highly selective and sensitive chemiluminescent immunoassay methods for field detection of the presence or amount of an analyte comprising chlorinated biphenyls in a sample solution. From the point of sample introduction, the assay has a five minute analysis time, a detection limit as low as about 1 part per billion (ppb) chlorinated biphenyl, and a working range of about three orders of magnitude which may be extended through appropriate sample addition.

The invention relates to a chemiluminescence method for detecting the presence or amount of an analyte comprising chlorinated biphenyls in a sample solution, the method comprising the steps of: incubating in a test container the sample solution, an analyte-specific antibody, and a probe conjugate for a time sufficient to form analyte-antibody complexes and probe conjugate-antibody complexes; removing non-complexed probe conjugates by washing the test container with a rinse solution selected from the group consisting of water, a buffer solution, and a surfactant solution; adding a chemiluminescence reagent to the test container; and measuring an intensity of light by an excited state of the chemiluminescence reagent to determine the presence or amount of chlorinated biphenyls in the sample.

This invention also provides a chemiluminescence method for detecting the presence or amount of an analyte comprising chlorinated biphenyls in a sample solution comprising the steps of: coating a test container with a binder, an analyte-specific antibody, and a probe conjugate; then admixing a sample solution to said test container for a time sufficient to form analyte-antibody complexes whereby the analyte displaces the probe conjugate from a site on the antibody; rinsing the test container with a rinse solution selected from the group consisting of water, a buffer solution, and a surfactant solution to wash away non-complexed probe conjugates; adding a chemiluminescence reagent to the test container; and measuring an intensity of light by an excited state of the chemiluminescence reagent to determine the presence or amount of chlorinated biphenyls in the sample solution.

This invention further provides a chemiluminescence method for the detection of the presence or amount of an analyte comprising chlorinated biphenyls in a sample solution comprising the steps of: coating a test container with a binder and an analyte-specific antibody; admixing in the test container the sample solution and a known concentration of a probe conjugate; incubating said admixture in the test container for a time sufficient to form analyte-antibody complexes and probe conjugate-antibody complexes whereby the analyte and probe conjugate compete for a site on the antibody; washing the test container with a rinse solution selected from the group consisting of water, a buffer solution, and a surfactant solution to remove non-complexed probe conjugates; adding a chemiluminescence reagent to the test container; and measuring an intensity of light emitted by an excited state of the chemiluminescence reagent to determine the presence or amount of chlorinated biphenyls in the sample.

The invention is particularly adapted for the detection of lightly chlorinated biphenyl compounds, i.e., low chlorine-content polychlorinated biphenyls. Lightly chlorinated biphenyl compounds mean molecules having about five or less chlorine atoms per biphenyl. Examples of commercial materials falling in this classification are Aroclors 1232, 1242, 1016, and 1221, and the like.

Additionally, the claimed methods are enzyme-linked chemiluminescence methods. One method relies on a displacement mode where the analyte displaces the probe conjugate from the complexing site on the analyte-specific antibody. In a subsequent step, the bound, residual probe conjugate catalyzes the decomposition of a chemiluminescent reagent, yielding an amount of light inversely related to the concentration of the chlorinated biphenyls in the sample. The amount of light generated can be measured using a luminometer or film.

Another method of this invention relies on a competitive mode instead of the displacement mode described above. In the competitive mode, the analyte and the probe conjugate are admixed together with the analyte-specific antibody. They contemporaneously compete for an antibody site to form a complex with the antibody.

There are several advantages of the invention over existing polychlorinated biphenyl immunoassay tests. One such advantage is high sensitivity to lower chlorinated biphenyl compounds, including low chlorinated polychlorinated biphenyls.

Antibodies used in commercially available kits are more reactive to polychlorinated biphenyl mixtures with high chlorine content. The antibodies of this invention were developed using a mono-chlorinated hapten, resulting in sensitivity to lower chlorinated polychlorinated biphenyl congeners. This is of particular importance in applications where anaerobic dechlorination has occurred.

Another advantage is short analysis time. For liquid samples, the total analysis will take less than ten minutes. This can include quantitative determination of chlorinated biphenyl content. The accurate determination of the amount of light generated during the reaction can be translated to chlorinated biphenyl concentrations relative to calibration standards run alongside samples.

A further advantage is that by using antibodies which selectively bind to different chlorinated biphenyl structural categories, such as lightly chlorinated, heavily chlorinated, planar, and non-planar structures, it is possible to generate a fingerprint response of an unknown sample which will be characteristic of a given polychlorinated biphenyl commercial product or altered polychlorinated commercial product. A similar approach can be used to analyze a specific or a group of specific congeners that may possess important chemical or biochemical properties. The analysis may be indicative as to the occurrence, development, or completion of a remedial process.

Still another advantage is that luminescence measurement is simple and no light source is required. The feature provides the unique advantage to measure multiple samples simultaneously. Thus, this invention provides the necessary field portability for efficient chlorinated biphenyl analysis on-site.

This invention also provides field portable kits for the above-mentioned displacement method and the competitive method.

DESCRIPTION OF THE INVENTION

This invention provides a glow-type chemiluminescence immunoassay for rapidly detecting the presence or amount of chlorinated biphenyls in a sample. An extraction step may be performed on the sample prior to analysis. Additionally, the invention can be practiced using a displacement method where the analyte displaces the probe conjugate at the antibody complexing site, or a competitive method where the analyte and probe conjugate compete for the antibody complexing site. Herein, the invention is described in terms of the displacement method. Attention will be drawn to the competitive method when such method differs from the displacement method.

The following definitions are applicable to the present invention. The term "sample solution", as used herein, refers to a sample in solution that is to be tested for the presence or amount of the analyte of interest. The sample may be a liquid or a solid. If it is a solid, such as soil, gravel, sand, pulverized concrete, sludge, and the like, an extraction step using an appropriate liquid may be performed on the sample. Such extraction methods for chlorinated biphenyls are known by those skilled in the art.

The term "analyte", as used herein, refers to a molecule whose presence or amount is being detected in the sample solution. Also, an analyte is a molecule that is reactive to analyte-specific antibodies and binds to a site on the antibody. Specifically, the analyte in this invention comprises chlorinated biphenyls of the following structure:

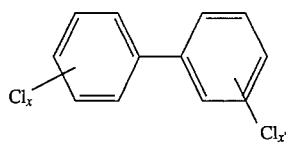

where x=1–5, x'=0–5, and x+x'≦5. Such an analyte comprises a group of related congeners from mono to pentachlorobiphenyl. The analyte is a protein-free compound. Additionally, the analyte does not induce antibody formation when injected into an animal but is reactive with analyte-specific antibodies.

The term "analyte-specific antibody", as used herein, refers to an antibody that binds the above-mentioned analyte at a binding site on the antibody. When the analyte-specific antibody and the analyte come in contact, the attachment of the antibody and analyte are herein referred to as a analyte-antibody complex.

Polyclonal antibodies for such an analyte typically are raised by first conjugating a hapten molecule to a protein carrier and then injecting the hapten conjugate into a receptive host, such as an animal. A rabbit is an example of a receptive host. The resulting analyte-specific antibodies that form in the host can be isolated in serum by conventional, well-known antibody isolation techniques.

Monoclonal antibodies can be raised by methods known to those skilled in the art.

The term "hapten", as used herein, refers to a molecule which is a chlorinated biphenyl analog. The hapten molecule is conjugated to a protein carrier to form a hapten conjugate molecule, which subsequently is injected into a receptive host to form analyte-specific antibodies. The hapten and hapten conjugate developed for this method are the subject of a copending, and commonly assigned patent application, entitled "Hapten And Hapten Conjugates For Immunoassay Technology".

The term "determinant", as used herein, refers to those regions of the analyte which are involved in specific binding reactions between analytes and antibodies.

The term "probe conjugate", as used herein, refers to the conjugation product of a probe molecule with a tag species.

The "probe molecule", as used herein, refers to a molecule which shares certain structural and electrostatic properties with the analyte of interest. Such a probe molecule is a protein-free compound. The probe conjugate and the analyte contain similar features which allow them to compete for a binding site on an analyte-specific antibody. In addition, the probe molecule can be modified such that it is not identical to the analyte while retaining the necessary determinant(s) for binding of the probe conjugate to an analyte-specific antibody. The probe molecule and the probe conjugate developed for this method are the subject of a copending, commonly assigned patent application entitled "Probe Conjugates For Immunoassay Technology".

The term "tag species", as used herein, refers to a chemical species that is conjugated to the probe molecule. There are four main types of tag species: enzymes, radiolabelled species, fluorescent molecules, and metal-labeled complexes. In this invention the tag species is an enzyme, which is responsible for catalyzing a chemical reaction which produces a detectable light signal. Other chemical species that catalyze a chemical reaction that produces a light signal may also be tag species in this invention.

When the analyte-specific antibody and the probe conjugate come in contact, the attachment of the antibody with the probe conjugate are herein referred to as probe conjugate-antibody complexes. Likewise, the probe conjugates that do not attach to the antibody when analytes are present, are herein referred to as non-complexed probe molecules.

The term "test container", as used herein, refers to a solid support material that is coated with the analyte-specific antibody. The solid support can be the well interiors of a microwell plate, modified glass slide, plastic surfaces, and the like.

The term "chemiluminescence reagent", as used herein, refers to a chemical that produces an emission of light from an excited state, without appreciable temperature increase.

In accordance with the method of the present invention, a mixture of haptens, low-chlorinated biphenyl analogues, are synthesized and used to generate analyte-specific antibodies. The antibodies are immobilized onto a solid surface of the test container, such as the well interiors of a microwell plate or modified glass slide. A binder, such as protein A, is used as an in-situ antibody purification medium and binds the antibody on the solid surface. In the competitive mode of this invention, the test container with the immobilized analyte-specific antibodies may be stored for a few weeks, under conditions common to those skilled in immunoassay technology, until the operator is ready to run a test of a sample solution.

In the competitive mode of this invention, when the operator runs a test of a sample solution, the test container with the immobilized antibodies is treated simultaneously with the probe conjugate, alkaline phosphatase bromobiphenyl, and a sample solution containing the analyte. During a short incubation period, the analyte molecules compete with the probe conjugate molecules for antibody complexing sites.

The competitive mode can also be practiced by sequential additions of the sample solution with a short incubation period, followed by the addition of a known amount of the probe conjugate with an incubation period. This type of competitive mode may be referred to as a sequential competitive method. Also, the probe conjugate with a short incubation period may precede the addition of the sample solution. It is a matter of preference for one operating the invention as to which order sequential additions of sample solution and probe conjugate are added to the test container. In the invention, a short incubation period is a time sufficient for the analyte or probe conjugate to complex at the analyte-specific antibody site.

The above-mentioned incubation periods are followed with rinses. After rinsing with a rinse solution selected from the group consisting of water, a buffer solution, and a surfactant solution, to remove non-complexed molecules, the chemiluminescent reagent, based on adamantyl dioxetane phosphate derivatives, is added to the test container. The reagent is catalytically decomposed by the remaining complexed probe conjugates with the concurrent generation of light.

The amount of light generated, which can be measured in a number of ways, is related to the concentration of chlorinated biphenyls in the original sample. The higher the chlorinated biphenyl concentration in the test solution, the fewer probe conjugates will be bound to the antibodies and the weaker the chemiluminescent signal that will be generated.

The displacement mode according to this invention also has immobilized analyte-specific antibodies bound on the solid support test container with protein-A. The displacement method differs from the competitive methods in that the probe conjugate is added to the test container prior to field operations. By so doing, the probe conjugate occupies the available complexing sites on the antibodies. At this point, the prepared test container with probe conjugate-antibody complexes can be stored for up to a few weeks until the test containers are needed to run sample solutions. The storage conditions are those utilized by one skilled in the art.

For a chlorinated biphenyl immunoassay to be successful, it must have effective analyte-specific antibodies. Many processes are involved in the antibody preparation. For instance, the selection of the haptens is critical because their structure determines the selectivity and binding strength of the resulting antibodies. Since there are 209 polychlorinated biphenyl congeners, it is difficult to generate an antibody that will bind to only one congener and have no crossreactivity to the others. It is also difficult to generate an antibody that will recognize all polychlorinated congeners. Thus, for a polychlorinated biphenyl site characterization, a mixture of antibodies which have reactivity for a certain blend of chlorinated biphenyl congeners is needed. One aspect of this invention is the generation of analyte-specific antibodies which will react favorably with lightly chlorinated biphenyls such as the Aroclors 1221, 1232, 1016, and 1242.

The haptens used in the production of the analyte-specific antibodies for this invention are a mixture of chlorinated biphenyl carboxylic acids, having the general structure

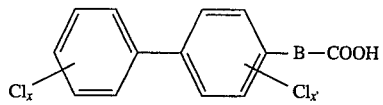

wherein $x=1–5$, $x'=0–4$, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring.

In particular, monochlorobiphenyl carboxylic acids were synthesized by a known phase transfer catalyzed radical coupling reaction between 4-carboxyethylbenzenediazonium tetrafluoroborate and chlorobenzene, followed by hydrolysis. The product was analyzed by gas chromatography and mass spectrometry and found to consist of about 85% 2'-chloro-4-biphenylcarboxylic acid and about 7–8% each of 3'- and 4'-chlorobiphenylcarboxylic acid. This material was used in the preparation of the analyte-specific antibodies of this invention. The molecular structure and composition of this hapten mixture are given below.

2'-chloro-4-biphenylcarboxylic acid (85%)

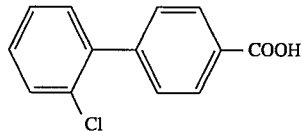

3'-chloro-4-biphenylcarboxylic acid (8%)

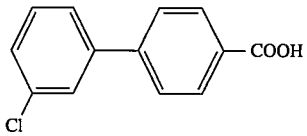

4'-chloro-4-biphenylcarboxylic acid (7%)

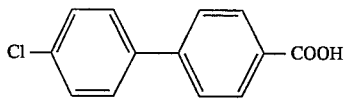

Since the above-mentioned haptens are too small to provide immunoresponse, they are conjugated to a carrier protein. This is the next step in manufacturing analyte-specific antibodies.

Illustrative protein carriers are bovine serum albumin, keyhole limpet hemocyanin (KLH), egg ovalbumin, thyroglobulin, bovine gamma globulin, and the like. A suitable protein carrier is keyhole limpet hemocyanin.

The following structure is representative of the hapten conjugate developed for manufacturing analyte specific antibodies.

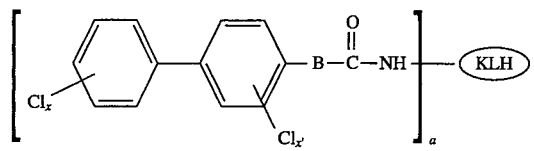

wherein $x=1–5$, $x'=0–4$, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and $a \geq 1$.

In making the hapten conjugate of the present invention, the chemical bonds between the carboxyl group attached to haptens and the amino groups on a carrier protein can be established using a variety of methods known to those skilled in the art.

The next step in preparing the analyte-specific antibodies of this invention is administering the hapten conjugate into a receptive host, such as a rabbit, to develop a response. The end result is that the appropriate antibodies are formed and selected according to methods well known to those skilled in the art. Although rabbits were the hosts used in the example described herein, any in vivo host capable of producing analyte-specific antibodies to the hapten conjugate can be used. Additionally, both polyclonal and monoclonal antibodies can be utilized in the practice of this invention.

In this invention the assay relies on the binding strength of chlorinated biphenyl molecules and the probe conjugates to bind these molecules at the analyte-specific antibody complexing sites. The selection of the right probe molecules to be linked to the tag species is important. The relative binding strength of the probe conjugate to the antibody and its reversibility for binding should be comparable to that of the analyte.

It has been discovered that brominated biphenyl carboxylic conjugates are capable of binding to the analyte-specific antibody complexing site, but can still be displaced from the site by chlorinated biphenyls. An example of such a probe molecule that provides the required binding strength is 4'-carboxy-4-bromobiphenyl.

Brominated biphenyl carboxylic acids are synthesized by standard techniques known to those skilled in the art. The general structure for the brominated biphenyl carboxylic acid is:

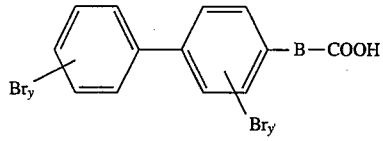

where $y=1–5$, $y'=0–4$, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring.

Both 4'-carboxy-4-bromobiphenyl (4'C4BB) and 4'-amino-4-bromobiphenyl (4'A4BB) have been tested in the claimed chemiluminescent assay as probe molecules. The structures for 4'C4BB and 4'A4BB are:

4'-carboxy-4-bromobiphenyl (4'C4BB)

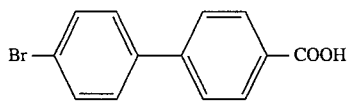

4'-amino-4-bromobiphenyl (4'A4BB)

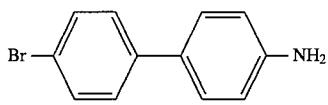

In this invention the probe molecule is conjugated to the tag species to form the probe conjugate. There are four main types of tag species: enzymes, radiolabelled species, fluorescent molecules, and metal-labeled complexes. Generally an enzyme is used as the tag species in this invention. The general structure for the probe conjugate is:

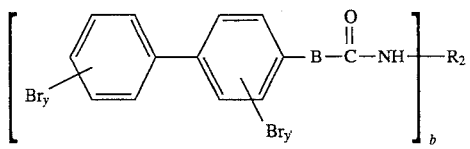

where y=1–5, y'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, $b \geq 1$ and $NH\text{-}R_2$ is the tag species.

To demonstrate the probe conjugate, the above-mentioned brominated compounds, 4'-carboxy-4-bromobiphenyl and 4'-amino-4-bromobiphenyl, are conjugated to the enzyme alkaline phosphatase (AP), which serves as the tag species, through the bifunctional linker, 1-ethyl-3-(3-dimethyl-aminopropyl) carbodiimide hydrochloride (EDC) by methods known to those skilled in the art. The structures for the probe conjugates are:

4'-carboxy-4-bromobiphenyl alkaline phosphatase (4'C4BB-AP)

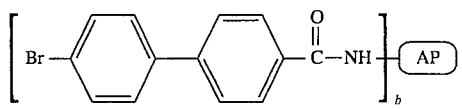

4'-amino-4-bromobiphenyl alkaline phosphatase (4'A4BB-AP)

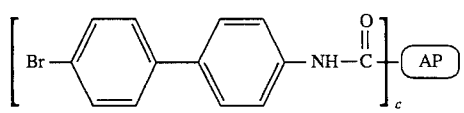

where $c \geq 1$.

It has been discovered that although 4'-carboxy-4-bromobiphenyl does not bind by itself to the analyte-specific antibodies in pH 7 buffer solution, its alkaline phosphatase conjugate, 4'-carboxy-4-bromobiphenyl alkaline phosphatase, interacts strongly with the analyte-specific antibodies of this invention. Conversely, it has also been discovered that 4'-amino-4-bromobiphenyl binds well to the analyte-specific antibodies, while its conjugate, 4'-amino-4-bromobiphenyl alkaline phosphatase, shows very weak affinity toward the antibodies.

Small chemical changes in the probe conjugate have been found to have dramatic effects on the performance of the assay. This is illustrated in Table 1., which compares assay performance using the two chemically similar probe conjugates, 4'-carboxy-4-bromobiphenyl and 4'-amino-4-bromobiphenyl alkaline phosphatase conjugates. The probe conjugate based on 4'-amino-4-bromobiphenyl alkaline phosphatase is ineffective in the assay in contrast to the probe conjugate 4'-carboxy-4-bromobiphenyl alkaline phosphatase. While the chemical constituents of these two probe conjugates are alike, the structures and electronic distribution may be very dissimilar due to different spacial arrangements of the carboxyl and amine conjugating groups on the tag species, alkaline phosphatase. This dramatic effect of small changes in molecular structure on analyte-specific antibody interaction with probe conjugates enables one to manipulate the relative competiveness of chlorinated biphenyls with the probe conjugates. It also provides flexibility in developing assays for different applications.

TABLE 1

EFFECT OF ALKALINE PHOSPHATASE CONJUGATE STRUCTURE ON ASSAY PERFORMANCE

| PCB in Methanol (Aroclor 1242) | 4'A4BB-AP INTENSITY | 4'C4BB-AP INTENSITY |
| --- | --- | --- |
| 44.0 ppm | 36.6 | 53.0 |
| 14.7 ppm | 36.2 | 57.2 |
| 4.4 ppm | 37.0 | 59.8 |
| 0.44 ppm | 36.3 | 69.1 |

Another step in this invention is coating the test container with the analyte-specific antibody. It has been found that the immobilization of the analyte-specific antibodies on the solid support of the test container can be achieved by incubating an analyte-specific antibody solution for a length of time, followed by thorough rinsing. The rinse solution is selected from the group consisting of water, a buffer solution, and a surfactant solution. The antibody solution can consist of diluted serum or only the IgG portion obtained from the serum via protein-A column purification.

IgG stands for immunoglobulin gamma and is the most abundant immunoglobulin in the serum. IgG consists of two pairs of polypeptide chains which are covalently linked by disulfide bonds. The antibody molecule has fragments, Fab and Fc. Fab, fragment antigen binding, binds univalently to chlorinated biphenyls or the probe conjugates. Fc, fragment crystallizable, is made from heavy chains and does not bind chlorinated biphenyls. Preferably, the Fc domain is bound to the solid support of the test container for proper orientation of the analyte-specific antibody.

It has been found that precoating the solid support with protein-A substantially increases the assay sensitivity and eliminates the requirement of antibody serum purification. Protein A selectively binds to the Fc domain of the antibodies, providing an excellent arrangement for analyte-specific antibody surface orientation.

Streptococcal protein-A pretreatment of the solid support is the preferred method for the practice of the invention. Table 2 shows the differences in assay response using analyte-specific antibody serum with and without protein-A treatment. Tests run with analyte-specific antibody serum on solid supports precoated with protein-A are comparable to tests run in a similar manner using purified IgG. Without protein-A pretreatment, the serum gave unacceptable results. This implies that protein-A is capable of serving as an in-situ serum purification procedure, while aligning the analyte-specific antibody surface. The assay in Table 2 was performed at 20° C. using a Packard Viewplate. The intensity, in arbitrary units, was obtained by digitizing film images taken, using a 50 second exposure with a Polaroid instant film (type 667).

TABLE 2

EFFECT OF PROTEIN-A PRECOATING ON ASSAY PERFORMANCE

| PCB in Methanol (Aroclor 1232) | Serum + Protein-A Intensity | IgG + Protein-A Intensity | Serum Intensity |
|---|---|---|---|
| 44.0 ppm | 33 | 34 | not detected |
| 4.4 ppm | 55 | 50 | not detected |
| 0.44 ppm | 65 | 58 | not detected |

Using the displacement method a sample solution is introduced into the test container, and after a sufficient amount of time is allowed for the chlorinated biphenyls to displace the probe conjugate from the antibody binding site, the test container is washed with a rinse solution to remove non-complexed probe conjugates. The rinse solution is selected from the group consisting of water, a buffer solution, and a surfactant solution. Following rinsing, a chemiluminescent reagent is added to the test container. The reagent is catalytically decomposed by the bound alkaline phosphatase and the excited state of the chemiluminescent reagent emits light which is measurable.

It should be noted that when using the competitive method of this invention, the sample solution and probe conjugate are added either simultaneously to the test container or sequentially. Both the analyte and the probe conjugate compete for antibody binding sites. After a sufficient amount of time for the molecules to react with the antibody, the test container is washed with water. The method then continues the same as the displacement method.

Selection of the chemiluminescent reagent depends on four factors: luminescence intensity; response time; reagent stability; and impact on the portable analysis. An example of an appropriate chemiluminescence reagent is adamantyl 1,2-dioxetane phosphate derivatives such as AMPPD (disodium 3-(4-methoxylspiro [1,2-dioxetane-3,2'-tricyclo-[3.3.1.1$^{3,7}$]decan]-4-yl) phenyl phosphate), which are commercially available. The chemiluminescent decomposition mechanism for AMPPD in water is given below.

Hydrolytic phosphate cleavage by alkaline phosphatase initiates the decomposition of AMPPD by releasing the electron-rich dioxetane phenolate. Charge transfer from the phenolates to the dioxetane ring promotes concerted breakdown of the cyclic peroxide and generates an electronically excited species. The species gives off light at 477 nm upon conversion to the ground state.

A modified AMPPD system under the trade name of Lumi-Phos 530, commercialized by Lumigen, Inc., can also be used in the assay. Lumi-Phos 530 offers better thermal stability and produces much higher emission output at 530 nm.

Generally, the light produced from an AMPPD system increases gradually to a plateau in about 1.5 hours and diminishes to undetectable amounts in about 8–10 hours. For the purpose of this method, measuring the rate at which light is generated in the first 5–10 minutes is sufficient to allow discrimination of samples from about 0.5–50 ppm chlorinated biphenyls.

The chemiluminescence produced by the assay can be detected using different devices, such as a commercial plate luminometer (model ML 3000 Dynatech), a camera (Camlight 501, Analytical Luminescence Laboratory) equipped with instant print film (Type 667, Polaroid Corp.), or other optical detection instruments. The chemiluminescence intensity increases with the increase of the detection temperature up to about 45°–50° C. due to the increase of enzyme activity. Visually inspecting the brightness of the film images gives a qualitative measure of PCB concentration, which in many cases is sufficient for field screening. Quantitative analysis can be achieved using a luminometer or by digitizing the images with a film reader (Model 1024, Clemecs Technology Inc.).

An advantage of the claimed method is that it is field portable. Operations that are done on site include sample extractions from particulate materials, such as soil, sand, sludge, dirt, gravel, pulverized concrete, and the like; sample solution introduction to the assay; incubation; washing; chemiluminescence reagent introduction; and light measurement. The steps prior to sample introduction can be done during the manufacture of the solid support or assay plate.

The assay of the present invention is performed in accordance with the following general procedure as an example when a 96-well microtiter plate is used. The procedure is broken into two sections: pre-site preparation and site application.

About one hundred microliters of 0.01 milligrams per milliliter of protein-A solution is added to each well of a

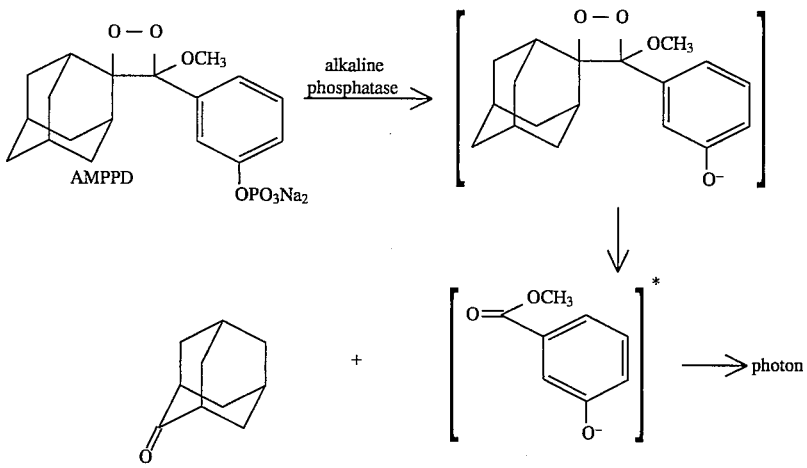

96-well plate and incubated at room temperature for at least one hour. Following incubation, each well is rinsed sufficiently with water, a buffered solution, or a surfactant solution to remove any excess protein-A solution. The rinsing can be repeated six times or more if necessary.

About one hundred microliters of diluted analyte-specific antibody serum solution (about 100-fold dilution with pH 7 PBS buffer from the straight serum) or about one hundred microliters of 0.03 milligrams per milliliter purified IgG analyte-specific antibody are added to each well and incubated for at least one hour at room temperature. Again each well is sufficiently rinsed with water, a buffer solution, or a surfactant solution to remove analyte-specific antibody solution that does not coat on the well interior surface. The rinsing can be repeated six times or more if needed.

Then, about one hundred microliters of 1.5 micrograms per milliliter of bromobiphenyl alkaline phosphatase conjugate solution (pH about 9.1 Tris buffer) are added to each well, followed by incubation for at least 30 minutes at room temperature. Each well is rinsed with water, a buffered solution, or a surfactant solution so that any excess non-complexed probe conjugate is removed. The rinsing can be repeated six times or more if necessary.

At this point, the plate can be stored in the refrigerator for future use. Plates have been stored for three weeks without diminishing assay activity. Plates can be stored longer based on the compositions and conditions applied.

At the field site, chlorinated biphenyls entrapped in particulate material are first extracted into a solution by methods known to those skilled in the art. Then, when using the displacement method, about one hundred microliters of the sample solution are added to each well and incubated for 2–10 minutes.

It should be noted that the sample solution can be further diluted before it is tested. For example, 10 microliters of the sample solution and about 90 microliters of PBS buffer solution can makeup the final sample solution. Dilutions of the sample solution can be made up to 100-fold.

Further, because of the large amount of wells available, samples can be run in replicates along with standard chlorinated biphenyl solutions to minimize the effects of experimental variations.

Each well is rinsed with a solution selected from the group consisting of water, a buffer solution, and a surfactant solution, so as to remove non-complexed probe conjugates after the incubation period.

Subsequently, about one hundred microliters of Lumiphos 530 reagent is added to each well and light intensity measurements are taken.

In addition to the above-mentioned procedure, another approach utilizing the claimed method, involves a direct competitive adsorption assay in which the analyte-specific antibody that is coated on the solid surface of the test container is exposed simultaneously to a sample solution and the probe conjugate. They compete for binding sites on the antibody. The lower the chlorinated biphenyl concentration in the sample, the more the probe conjugate binds to the surface and the stronger the chemiluminescence signal.

The assay has been successfully demonstrated. Table 3 shows the chemiluminescence intensities for polychlorinated biphenyls in Aroclor 1242 and 1232 solutions with methanol at four different concentrations, 0.44, 4.4, 14.7, and 44 ppm.

The actual polychlorinated biphenyl concentration in the assay is 50 times less due to dilution into an assay buffer. Buffer solutions are generally used since organic solvents can potentially denature the analyte-specific antibodies. The buffer dilution factor can be varied from about 4 to 50 fold without affecting the assay performance.

The assay results from Table 3 were performed with a Dynatech Microlite-2 plate at 40° C. The chemiluminescence intensity was measured with a Dynatech plate luminometer using an integration time of 60 seconds.

TABLE 3

CHEMILUMINESCENCE INTENSITY VERSUS PCB CONCENTRATION

| PCB in $CH_3OH$ | Intensity Aroclor 1242 | Intensity Aroclor 1232 |
| --- | --- | --- |
| 44.0 ppm | 53.0 | 56.8 |
| 14.7 ppm | 57.2 | — |
| 4.4 ppm | 59.8 | 62.2 |
| 0.44 ppm | 69.1 | 67.1 |

As demonstrated by the above table, the higher the chlorinated biphenyl concentration, the lower the amount of light generated.

The effect of methanol concentration on assay performance has been studied. The assay is more effective when methanol concentrations range from about 2–25 volume percent. Methanol content below 2% by volume yields large variation in final results and methanol content above 25% by volume greatly diminishes the assay's sensitivity. Table 4 shows the effect of 5% and 10% methanol concentration of PCB samples on assay performance. The intensity, in arbitrary units, was obtained by digitizing the film images. A Dynatech Immulon-4 plate was used at 20° C. The results demonstrated that the chemiluminescent intensity only responds to the chlorinated biphenyl concentration and that the methanol content in the sample solution has no effect on the light intensity.

TABLE 4

EFFECT OF METHANOL CONCENTRATION ON ASSAY PERFORMANCE

| Aroclor 1232 in $CH_3OH/H_2O$ | 10% $CH_3OH$ Intensity | 5% $CH_3OH$ Intensity |
| --- | --- | --- |
| 0.005 ppm | — | 46.5 |
| 0.010 ppm | 43.1 | — |
| 0.050 ppm | — | 36.1 |
| 0.10 ppm | 30.2 | — |
| 0.50 ppm | — | 21.6 |
| 1.00 ppm | 18.5 | — |
| 2.50 ppm | — | 10.6 |
| 5.00 ppm | 9.6 | — |

The following examples further demonstrate the invention.

EXAMPLE 1. Synthesis of hapten mixture of monochloro-biphenyl carboxylic acids.

A 250 milliliter round bottom flask equipped with a Teflon-coated magnetic stir bar and gas inlet and outlet tubes was flushed with nitrogen and charged with 4-carboxyethylbenzenediazonium tetrafluoroborate (7.92 grams, 0.03 mole), 18-crown-6 (0.40 grams, 0.0015 mole) and 100 milliliters chlorobenzene.

Stirring was started, and anhydrous potassium acetate (5.89 grams, 0.06 mole) was added in a single batch. The reaction grew warm to the touch and turned red-brown. After 2.5 hours, the reaction was filtered and the filtrate was washed with saturated sodium chloride solution and with water. The organic layer was dried over sodium sulfate, filtered, and evaporated. The residue was chromatographed on silica gel using methylene chloride as the elutant.

Fractions 5–9 (50 milliliter fractions were collected) were combined and evaporated yielding a mixture of chlorobiphenylcarboxylate esters as a yellow oil (2.15 grams, 30%). High pressure liquid chromatograph analysis (70% CH₃CN/ 30% H₂O, isocratic, C-18 column) indicated three isomers making up ~97% of the mixture.

The oil was transferred to a 250 milliliter round bottom flask equipped with a water-cooled condenser. Potassium hydroxide solution (30 milliliters, 2N) and absolute ethanol (30 milliliters) were added. The suspension was refluxed for five hours, cooled and filtered. A solid was recovered (A). The filtrate was acidified with hydrochloric acid and the resulting precipitate was recrystallized from ethanol/water.

This process produced a white solid (0.11 grams, melting point 223°–239° C.). The product was analyzed by gas chromatography-mass spectrometry and found to consist of about 84% 2'-chloro-4-biphenylcarboxylic acid and 7–8% each of 3'- and 4'-chlorobiphenyl-carboxylic acid. This material was used in the preparation of analyte-specific antibodies. Additional product, though less pure, was isolated by dissolving solid (A) in water and acidifying with HCl. The resulting precipitate after being filtered and recrystallized from ethanol/water yielded a white solid (1.14 grams, melting point 206°–216 C.).

EXAMPLE 2. Generation of analyte-specific antibodies.

Analyte-specific antibodies were generated in a three step process. A chlorinated biphenyl-like hapten, such as monochlorobiphenyl carboxylic acid as a mixture of three isomers, was synthesized. This mixture was conjugated to keyhole limpet hemacyanin using EDC (1-ethyl-3-(3-dimethylaminopropyl)carbodiimide hydrochloride). Polyclonal analyte-specific antibodies were produced in rabbits and isolated from serum using a standard protocol known in the skill of the art. A total of fifteen serum batches were harvested and characterized, and the three high quality serum batches were pooled together and stored in a deep freeze in 1 milliliter aliquots.

The antibody serum was tested for its response to different Aroclors using an enzyme linked immunosorbant assay. It was found that the antibodies made with the monochlorobiphenyls of the instant invention are more reactive to the lightly chlorinated Aroclors, while the commercially available immunoassays containing antibodies are more reactive toward the heavily chlorinated Aroclors.

EXAMPLE 3. Probe conjugates for chlorinated biphenyl chemiluminescence immunoassay.

Presented below are two brominated biphenyl molecules which have been tested for chlorinated biphenyl chemiluminescence immunoassay. They were conjugated to alkaline phosphatase through a bifunctional linker, EDC (1-ethyl-3-(3-dimethylaminopropyl(carbodiimide hydrochloride).

4'-carboxy-4-bromobiphenyl (4'C4BB)

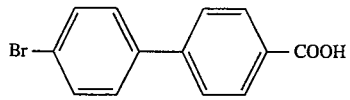

4'-carboxy-4-bromobiphenyl alkaline phosphatase (4'C4BB-AP)

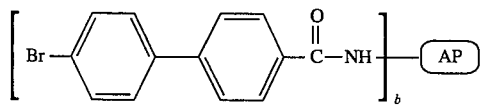

4'-amino-4-bromobiphenyl (4'A4BB)

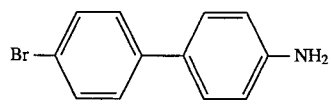

4'-amino-4-bromobiphenyl alkaline phosphatase (4'A4BB-AP)

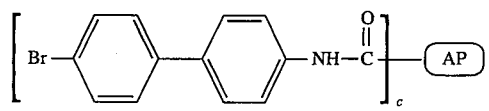

EXAMPLE 4. Experimental Procedure
A typical experimental procedure is as follows:

1. Add 100 microliters of protein-A solution (about 0.01 milligrams per milliliter in PBS buffer) to each well and incubate for about 3 hours.
2. Wash each well 6 times with Millipore water and aspirate dry.
3. Add 100 microliters of the diluted serum solution (about 100 time dilution of original serum with pH 7 PBS buffer) to each well and incubate for about 4 hours.
4. Wash each well 6 times with Millipore water and aspirate dry.
5. Add 100 microliters of 4'C4BB-AP (about 1.5 micrograms per milliliter in pH 9 Tris buffer) solution to each well and incubate for about 3 hours.
6. Wash each well 6 times with Millipore water and aspirate dry. Then store the plate at 4° C. overnight. Take the plate out one hour before the next step.
7. Add 100 microliters of sample solution (obtained by diluting the original solutions of 0.44, 4.4, 14.7, and 44 ppm polychlorinated biphenyls in methanol with pH 7 PBS buffer) to each well and incubate for about 2–15 minutes.
8. Wash each well 6 times with Millipore water and aspirate or shake dry.
9. Add 100 microliters of Lumi-Phos 530 solution to each well and take light intensity measurement.

What is claimed:

1. A chemiluminescence method for detecting a presence or an amount of an analyte comprising chlorinated biphenyls in a sample solution, the method comprising the steps of:

(a) incubating in a test container that is precoated with protein-A and precoated with an analyte-specific antibody, the sample solution and a probe conjugate, for a time sufficient to form analyte-antibody complexes and probe conjugate-antibody complexes, wherein the analyte-specific antibody is raised against a hapten conjugate, said hapten conjugate is produced by conjugating a protein to a hapten to form the hapten conjugate, the hapten having the structure:

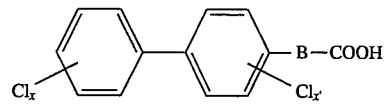

wherein x=1–5, x'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and wherein said hapten conjugate has the structure:

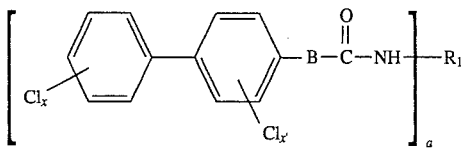

where x=1–5, x'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, a≧1, and NH-R$_1$ is a protein selected from the group consisting of bovine serum albumin, keyhole limpet hemocyanin (KLH), egg ovalbumin, thyroglobulin, and bovine gamma globulin, and wherein the probe conjugate is produced by linking a tag species that catalyzes a chemiluminescence reaction to a probe molecule having the structure:

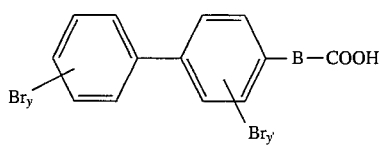

where y=1–5, y'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and where the probe conjugate has the structure:

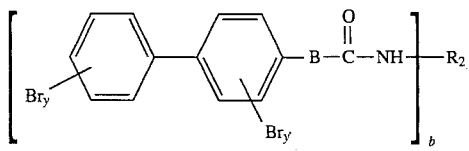

whrein y–1–5, y'=0–4, B is a bridge group consisting of from 0 to 20 carbon atoms and heteratoms, arranged in a straight or branched chain, saturated or unsaturated, where B is not a single heteroatom, branching occurs only on carbon atoms, and B is attached to a biphenyl ring, b≧1, and NH-R$_2$ is the tag species;

(b) removing non-complexed probe conjugates by washing the test container with a rinsing solution selected from the group consisting of water, a buffer solution, and a surfactant solution;

(c) then adding a chemiluminescence reagent to the test container; and (d) measuring an intensity of light emitted by an excited state of the chemiluminescence reagent to determine the presence or amount of chlorinated biphenyls in the sample.

2. A method according to claim 1 wherein the chlorinated biphenyls comprise the following structure

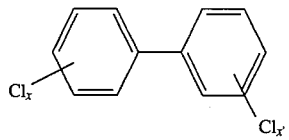

wherein x=1–5 and x'=0–5, with the proviso that together x and x' are ≦5.

3. A method according to claim 1 wherein the sample solution is prepared by performing an extraction procedure prior to step (a).

4. A method according to claim 1 wherein the hapten is a mixture consisting essentially of 2'-chloro-4-biphenylcarboxylic acid, 3'-chloro-4-biphenylcarboxylic acid, and 4'-chloro-4-biphenylcarboxylic acid.

5. A method according to claim 1 where x=1, x'=0, B=0, a≧1, and R$_1$ is keyhole limpet hemocyanin for said hapten conjugate.

6. A method according to claim 1 where the antibody is polyclonal or monoclonal.

7. A method according to claim 1 where y=1, y'=0, B=0, b≧1, and the tag species is alkaline phosphatase for said probe conjugate.

8. A method according to claim 1 wherein the chemiluminescence reagent is an adamantyl 1,2-dioxetane phosphate derivative.

9. A chemiluminescence method for detecting a presence or an amount of an analyte comprising chlorinated biphenyls in a sample solution, the method comprising the steps of:

(a) coating a test container with an antibody binder, an analyte-specific antibody, and a probe conjugate to form probe conjugate-antibody complexes, wherein the analyte-specific antibody is raised against a hapten conjugate, said hapten conjugate is produced by conjugating a protein to a hapten to form the hapten conjugate, the hapten having the structure:

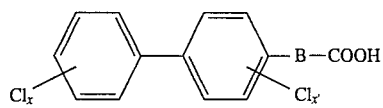

where x=1–5, x'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and wherein said hapten conjugate has the structure:

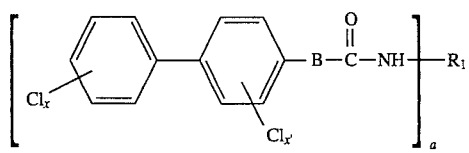

where x=1–5, x'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, a≧1, and NH-R$_1$ is a protein selected from the group consisting of bovine serum albumin, keyhole limpet hemocyanin (KLH), egg ovalbumin, thyroglobulin, and bovine gamma globulin, and wherein the probe conjugate is produced by linking a tag species that catalyzes a chemi-luminescence reaction to a probe molecule having the structure:

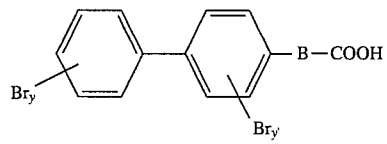

where y=1–5, y'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and where the probe conjugate has the structure:

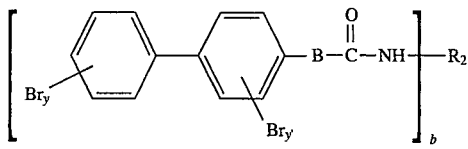

wherein y=1–5, y'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, b≧1, and NH-R$_2$ is the tag species;

(b) admixing a sample solution to said test container for a time sufficient to form analyte-antibody complexes whereby the analyte displaces the probe conjugate from a site on the antibody;

(c) rinsing the test container with a rinse solution selected from the group consisting of water, a buffer solution, and a surfactant solution to remove non-complexed probe conjugates;

(d) adding a chemiluminescence reagent to the test container; and (e) measuring an intensity of light emitted by an excited state of the chemiluminescence reagent to determine the presence or amount of chlorinated biphenyls in the sample solution.

10. A method according to claim 9 wherein the chlorinated biphenyls comprise the following structure

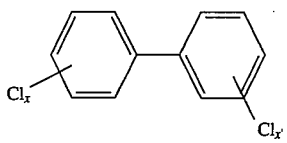

wherein x=1–5 and x'=0–5, with the proviso that together x and x' are≦5.

11. A method according to claim 9 wherein the sample solution is prepared by performing an extraction procedure prior to step (b).

12. A method according to claim 9 wherein the hapten is a mixture consisting essentially of 2'-chloro-4-biphenylcarboxylic acid, 3'-chloro-4-biphenylcarboxylic acid, and 4'-chloro-4-biphenylcarboxylic acid.

13. A method according to claim 9 where x=1, x'=0, B=0 carbons, a≧1, and R$_1$ is keyhole limpet hemocyanin for said hapten conjugate.

14. A method according to claim 9 where the antibody is polyclonal or monoclonal.

15. A method according to claim 9 where y=1, y'=0, B=0 carbon, b≧1, and the tag species is alkaline phosphatase for said probe conjugate.

16. A method according to claim 9 wherein the chemiluminescence reagent is an adamantyl 1,2-dioxetane phosphate derivative.

17. A method according to claim 9 wherein the antibody binder of step (a) is protein-A.

18. A kit for detecting the presence or amount of chlorinated biphenyls in a sample solution which kit comprises:

(a) a test container precoated with a binder, an analyte-specific antibody, and a probe conjugate, where the analyte-specific antibody is raised against a hapten protein conjugate, said hapten conjugate is produced by conjugating a protein to a hapten wherein said hapten protein conjugate has the structure:

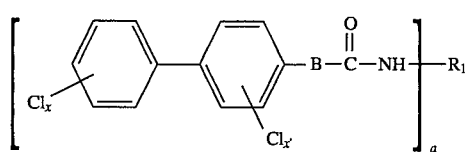

where x=1–5, x'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, a≧1, and NH-R$_1$ is a protein selected from the group consisting of bovine serum albumin, keyhole limpet hemocyanin (KLH), egg ovalbumin, thyroglobulin, and bovine gamma globulin, and where the probe conjugate has the structure:

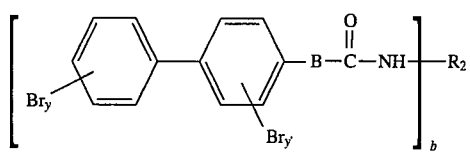

wherein y=1–5, y'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, b≧1, and NH-R$_2$ is a tag species, said tag species being an enzyme and capable of catalyzing a chemiluminescence reaction;

(b) a chemiluminescence reagent that is capable of being catalyzed by the tag species; and (c) a device to measure an intensity of light.

19. The kit according to claim 18 wherein the antibody of step (a) is polyclonal or monoclonal and the binder is protein-A.

20. The kit according to claim 18 wherein the chemiluminescence reagent is an adamantyl 1,2-dioxetane phosphate derivative.

21. A chemiluminescence method for detecting a presence or an amount of an analyte comprising chlorinated biphenyls in a sample solution, the method comprising the steps of:

(a) coating a test container with an antibody binder and an analyte-specific antibody, wherein the analyte-specific antibody is raised against a hapten conjugate, said hapten conjugaate is produced by conjugating a protein to a hapten to form the hapten conjugate, the hapten having the structure:

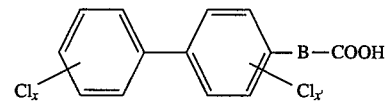

where x=1–5, x'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and wherein said hapten conjugate has the structure:

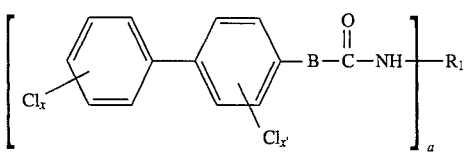

where x=1–5, x'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, a≧1, and NH-R₁ is a protein selected from the group consisting of bovine serum albumin, keyhole limpet hemocyanin (KLH), egg ovalbumin, thyroglobulin, and bovine gamma globulin;

(b) admixing in the test container the sample solution and a known concentration of a probe conjugate, wherein the probe conjugate is produced by linking a tag species that catalyzes a chemi-luminescence reaction to a probe molecule having the structure:

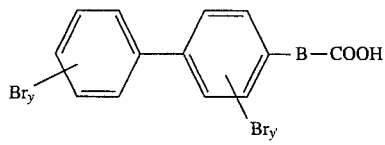

where y=1–5, y'=0–4, and B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, and where the probe conjugate has the structure:

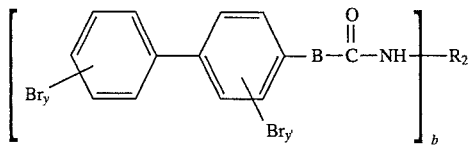

wherein y=1–5, y'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, b≧1, and NH-R₂ is the tag species;

(c) incubating said admixture in the test container for a time sufficient to form analyte-antibody complexes and probe conjugate-antibody complexes whereby the analyte and probe conjugate compete for a site on the antibody;

(d) washing the test container with a rinse solution selected from the group consisting of water, a buffer solution, and a surfactant solution;

(e) adding a chemiluminescence reagent to the test container; and (f) measuring an intensity of light emitted by an excited state of the chemiluminescence reagent to determine the presence or amount of chlorinated biphenyls in the sample.

22. A method according to claim 21 wherein the chlorinated biphenyls comprise the following structure

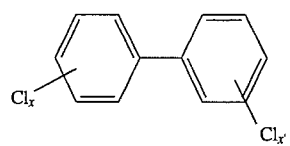

wherein x=1–5 and x'=0–5, with the proviso that together x and x' are ≦5.

23. A method according to claim 21 wherein the sample solution is prepared by performing an extraction procedure prior to step (b).

24. A method according to claim 21 wherein the hapten is a mixture consisting essentially of 2'-chloro-4-biphenylcarboxylic acid, 3'-chloro-4-biphenylcarboxylic acid, and 4'-chloro-4-biphenylcarboxylic acid.

25. A method according to claim 21 where x=1, x'=0, B=0 carbons, a≧1, and R₁ is keyhole limpet hemocyanin for said hapten conjugate.

26. A method according to claim 21 where the antibody is polyclonal or monoclonal.

27. A method according to claim 21 where y=1, y'=0, B=0 carbon, b≧1, and the tag species is alkaline phosphatase for said probe conjugate.

28. A method according to claim 21 wherein the chemiluminescence reagent is an adamantyl 1,2-dioxetane phosphate derivative.

29. A method according to claim 21 wherein the antibody binder of step (a) is protein-A.

30. A kit for detecting the presence or amount of chlorinated biphenyls in a sample solution which kit comprises:

(a) a test container precoated with a binder and an analyte-specific antibody, wherein the analyte-specific antibody is raised against a hapten conjugate, said hapten conjugate is produced by conjugating a protein to a hapten to form the hapten conjugate, wherein said hapten protein conjugate has the structure:

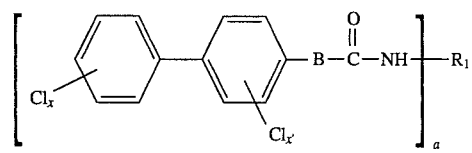

where x=1–5, x'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, a≧1, and NH-R₁ is a protein selected from the group consisting of bovine serum albumin, keyhole limpet hemocyanin (KLH), egg ovalbumin, thyroglobulin, and bovine gamma globulin;

(b) a known concentration of a probe conjugate where the probe conjugate has the structure

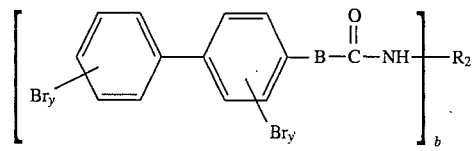

wherein y=1–5, y'=0–4, B is a bridge group consisting of from 0 to 20 carbon atoms and heteroatoms, arranged in a straight or branched chain, saturated or unsaturated, where B is not a single heteroatom, branching occurs only on carbon atoms, and B is attached to a biphenyl ring, $b \geq 1$, and $NH\text{-}R_2$ is the tag species, said tag species being an enzyme and capable of catalyzing a chemiluminescence reaction;

(c) a chemiluminescence reagent that is capable of being catalyzed by the tag species; and (d) a device to measure an intensity of light.

31. The kit according to claim 30 wherein the antibody of step (a) is polyclonal or monoclonal and the binder is protein-A.

32. The kit according to claim 30 wherein the chemiluminescence reagent is an adamantyl 1,2-dioxetane phosphate derivative.

* * * * *